(12) United States Patent
Flockerzi

(10) Patent No.: US 6,936,622 B2
(45) Date of Patent: Aug. 30, 2005

(54) 6-PHENYLBENZONAPHTHYRIDINES

(75) Inventor: Dieter Flockerzi, Allensbach (DE)

(73) Assignee: Altana Pharma AG, Constance (DE)

( * ) Notice: Subject to any disclaimer, the term of this patent is extended or adjusted under 35 U.S.C. 154(b) by 131 days.

(21) Appl. No.: 10/467,568

(22) PCT Filed: Feb. 21, 2002

(86) PCT No.: PCT/EP02/01819

§ 371 (c)(1),
(2), (4) Date: Aug. 8, 2003

(87) PCT Pub. No.: WO02/066476

PCT Pub. Date: Aug. 29, 2002

(65) Prior Publication Data

US 2004/0097537 A1 May 20, 2004

(30) Foreign Application Priority Data

Feb. 21, 2001 (EP) .......................... 01104086

(51) Int. Cl.[7] .............................. A61K 31/44
(52) U.S. Cl. ................. 514/292; 546/88; 546/81; 546/65; 544/126; 544/361; 514/232.8; 514/253; 514/287

(58) Field of Search ............... 514/292, 232.8, 514/253, 287; 546/88, 81, 65; 544/126, 361

(56) References Cited

U.S. PATENT DOCUMENTS 6,008,215 A * 12/1999 Flockerzi ............... 514/217.07

FOREIGN PATENT DOCUMENTS

| WO | WO 98/21208 | 5/1998 |
| WO | WO 98/40382 | 9/1998 |
| WO | WO 98/55481 | 12/1998 |
| WO | WO 99/57118 | 11/1999 |
| WO | WO 00/12501 | 3/2000 |

* cited by examiner

Primary Examiner—Charanjit S. Aulakh
(74) Attorney, Agent, or Firm—Nath & Associates PLLC; Todd L. Juneau; Sheldon M. McGee

(57) ABSTRACT

Compounds of the formula (I), in which R1, R2, R3, R4 and R5 have the meanings indicated in the description, are novel effective PDE3/4 Inhibitors.

16 Claims, No Drawings

6-PHENYLBENZONAPHTHYRIDINES

FIELD OF APPLICATION OF THE INVENTION

The invention relates to novel 6-phenylbenzonaphthyridines which are used in the pharmaceutical industry for the production of medicaments.

KNOWN TECHNICAL BACKGROUND

The international applications WO98/21208 (=U.S. Pat. No. 6,008,215), WO98/40382 (=U.S. Pat. No. 6,143,759), WO99/57118 (=U.S. Pat. No. 6,306,869) and WO00/12501 describe 6-phenylbenzonaphthyridines and their N-oxides as PDE3/4 inhibitors.

DESCRIPTION OF THE INVENTION

It has now been found that the compounds of the formula I, which are described in more detail below and which differ from the prior-art compounds in particular by substitution on the 6-phenyl ring, have surprising and particularly advantageous properties.

The invention thus relates to compounds of the formula I,

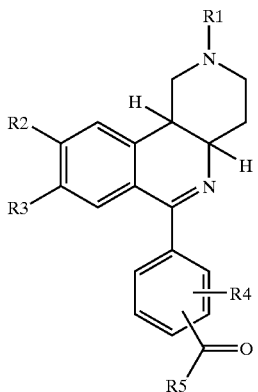

(I)

in which
R1 is 1–4C-alkyl,
R2 is hydroxyl, 1–4C-alkoxy, 3–7C-cycloalkoxy, 3–7C-cycloalkylmethoxy, or 1–4C-alkoxy completely or predominantly substituted by fluorine,
R3 is hydroxyl, 1–4C-alkoxy, 3–7C-cycloalkoxy, 3–7C-cycloalkylmethoxy, or 1–4C-alkoxy completely or predominantly substituted by fluorine,
or in which
R2 and R3 together are a 1–2C-alkylenedioxy group,
R4 is hydrogen, halogen, nitro, 1–4C-alkyl, trifluoromethyl or 1–4C-alkoxy,
R5 is a radical of the formula (a), (b) or (c)

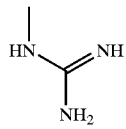

(a)

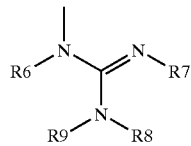

(b)

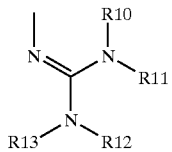

(c)

in which
if R5 is a radical of the formula (b),
either
R6, R7, R8 and R9 independently of one another are hydrogen, 1–7C-alkyl, 3–7C-cycloalky), 3–7C-cycloalkylmethyl or hydroxy-2–4C-alkyl,
or
R6 is hydrogen, 1–7C-alkyl, 3–7C-cycloalkyl, 3–7C-cycloalkylmethyl or hydroxy-2–4C-alkyl
R7 is hydrogen, 1–7C-alkyl, 3–7C-cycloalkyl, 3–7C-cycloalkylmethyl or hydroxy-2–4C-alkyl
R8 and R9, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1radical,
in which
if R5 is a radical of the formula (c),
either
R10, R11, R12 and R13 independently of one another are hydrogen, 1–7C-alkyl, 3–7C-cycloalky 3–7C-cycloalkylmethyl or hydroxy-2–4C-alkyl,
or
R10 and R11 independently of one another are hydrogen, 1–7C-alkyl, 3–7C-cycloalkyl, 3–7C-cycloalkylmethyl or hydroxy-2–4C-alkyl, and
R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1radical,
or
R10 and R11, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1radical, and
R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1radical,
or
R10 and R13 independently of one another are hydrogen or 1–4C-alkyl, and
R11 and R12, together and including the N—C(=)—N structure to which they are bonded, are a hexahydropyrimidin-2-ylidene or imidazolidin-2-ylidene radical,
the salts of these compounds, as well as the N-oxides, enantiomers, E/Z isomers and tautomers of these compounds and their salts.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1–4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned. In this context, "predominantly" means that more than half of the hydrogen atoms of the 1–4C-alkoxy groups are replaced by fluorine atoms.

1–2C-Alkylenedioxy represents, for example, the methylenedioxy (—O—CH$_2$—O—) or the ethylenedioxy (—O—CH$_2$—CH$_2$—O—) radical.

Halogen within the meaning of the invention is fluorine, chlorine or bromine.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radical.

3–7C-Cycloalkyl represents the cyclopropyl, cyclobutyl, cyclopentyl, cyclohexyl or cycloheptyl radical.

3–7C-Cycloalkylmethyl represents a methyl radical which is substituted by one of the abovementioned 3–7C-cycloalkyl radicals. Examples which may be mentioned are the cycloalkylmethyl radicals cyclopropylmethyl, cyclobutylmethyl and cyclopentylmethyl.

Hydroxy-2–4C-alkyl represents 2–4C-alkyl radicals which are substituted by a hydroxyl group. Examples which may be mentioned are the 2-hydroxyethyl and the 3-hydroxypropyl radicals.

The substituents R4 and —C(O)R5 of the compounds of the formula I can be attached in the ortho, meta or para position with respect to the binding position in which the 6-phenyl ring is bonded to the benzonaphthyridine ring system. Preference is given to compounds of the formula I, in which R4 is hydrogen and —C(O)R5 is attached in the meta or in the para position.

Suitable salts of compounds of the formula I—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand salts with bases are also suitable. Examples of salts with bases which may be mentioned are alkali metal (lithium, sodium, potassium) or calcium, aluminum, magnesium or titanium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

It is known to the person skilled in the art that the compounds according to the invention and their salts, for example when they are isolated in crystalline form, may comprise varying amounts of solvents. Accordingly, the invention also embraces all solvates and in particular all hydrates of the compounds of the formula I, and also all solvates and in particular all hydrates of the salts of the compounds of the formula I.

Compounds of the formula I to be emphasized are those in which

R1 is 1–4C-alkyl,

R2 is 1–4C-alkoxy, 3–6C-cycloalkoxy, 3–6C-cycloalkylmethoxy, or 1–4C-alkoxy which is or predominantly substituted by fluorine, R3 is 1–4C-alkoxy, 3–6C-cycloalkoxy, 3–6C-cycloalkylmethoxy, or 1–4C-alkoxy which is or predominantly substituted by fluorine, R4 is hydrogen, halogen, nitro, 1–4C-alkyl, trifluoromethyl or 1–4C-alkoxy, R5 is a radical of the formula (a), (b) or (c)

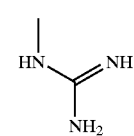

(a)

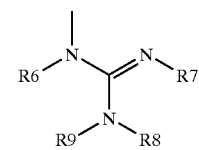

(b)

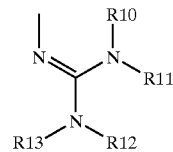

(c)

in which
if R5 is a radical of the formula (b),
either
R6 is hydrogen, and
R7, R8 and R9 independently of one another are hydrogen, 1–4C-alkyl, 3–7C-cycloalkyl, 3–7C-cycloalkylmethyl or hydroxy-2–4C-alkyl,
or R6 is hydrogen,
R7 is hydrogen, 1–4C-alkyl, 3–7C-cycloalkyl or 3–7C-cycloalkylmethyl, and
R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical, in which
if R5 is a radical of the formula (c),
either
R10, R11, R12 and R13 independently of one another are hydrogen, 1–4C-alkyl, 3–7C-cycloalky 3–7C-cycloalkylmethyl or hydroxy-2–4C-alkyl,
or
R10 and R11 independently of one another are hydrogen, 1–4C-alkyl, 3–7C-cycloalkyl, 3–7C-cycloalkylmethyl or hydroxy-2–4C-alkyl, and
R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical,
or
R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical, and
R12 and R13, together and including the nitrogen atom to which both are bonded, are a 1-pyrrolidinyl, 1-piperidinyl, 1-hexahydroazepinyl, 4-morpholinyl or 4-(1–2C-alkylypiperazin-1-yl radical,
or
R10 and R13 independently of one another are hydrogen or 1–4C-alkyl, and
R11 and R12, together and including the N—C(=)—N structure to which they are bonded, are a hexahydropyrimidin-2-ylidene or imidazolidin-2-ylidene radical, the salts of these compounds, as well as the N-oxides, enantiomers, E/Z isomers and tautomers of these compounds and their salts.

Compounds of the formula I to be particularly emphasized are those in which
R1 is methyl,
R2 is 1–4C-alkoxy,
R3 is 1–4C-alkoxy,
R4 is hydrogen,
R5 is a radical of the formula (a), (b) or (c)

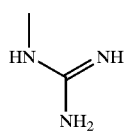

(a)

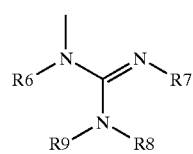

(b)

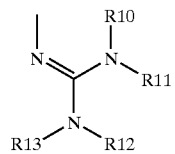

(c)

in which
if R5 is a radical of the formula (b),
either
R6 is hydrogen,
R7 is hydrogen, 1–4C-alkyl, 3–7C-cycloalkyl or 3–7C-cycloalkylmethyl,
R8 is hydrogen, 1–4C-alkyl, 3–7C-cycloalkyl or 3–7C-cycloalkylmethyl, and
R9 is hydrogen, 1–4C-alkyl or hydroxy-2–4C-alkyl,
where at least one of the radicals R7, R8 and R9 is not hydrogen,
or
R6 is hydrogen,
R7 is hydrogen, 1–4C-alkyl, 3–7C-cycloalkyl or 3–7C-cycloalkylmethyl, and
R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical,
in which
if R5 is a radical of the formula (c),
either
R10 is hydrogen or 1–4C-alkyl,
R11 is hydrogen, 1–4C-alkyl, 3–7C-cycloalkyl or 3–7C-cycloalkylmethyl,
R12 is hydrogen, 1–4C-alkyl, 3–7C-cycloalkyl or 3–7C-cycloalkylmethyl, and
R13 is hydrogen, 1–4C-alkyl or hydroxy-2–4C-alkyl,
where at least one of the radicals R10, R11, R12 and R13 is not hydrogen,
or
R10 is hydrogen or 1–4C-alkyl,
R11 is hydrogen, 1–4C-alkyl, 3–7C-cycloalkyl or 3–7C-cycloalkylmethyl, and
R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical,
or
R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical, and
R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1radical, the salts of these compounds, as well as the N-oxides, enantiomers, E/Z isomers and tautomers of these compounds and their salts.

Preferred compounds of the formula I are those in which
R1 is methyl,
R2 is methoxy or ethoxy,
R3 is methoxy,
R4 is hydrogen, R5 is N'-(N,N-dimethyl)guanidyl, N'-(N,N-diethyl)guanidyl, (morpholine)4-carboxamidinyl, 4-methylpiperazine-1-carboxamidinyl, N'-[N-(2-hydroxyethyl)-N-methyl]guanidinyl, N''-(N,N,N',N'-tetramethyl)guanidyl, N-guanidinyl, N'-(N,N,N''-trimethyl)guanidinyl, N-(N'-methyl)guanidinyl, N-(N'-isopropyl)guanidinyl, N-(N'-propyl)guanidinyl, N-(N'-isobutyl)guanidinyl, N-(N'-ethyl)guanidinyl, N-cyclohexyl-N'-guanidinyl, N-cyclohexylmethyl-N'-guanidinyl, N-buty-N'-guanidinyl or pyrrolidin-1-carboxamidinyl, the salts of these compounds, as well as the N-oxides, enantiomers, E/Z isomers and tautomers of these compounds and their salts.

The compounds of the formula I are chiral compounds having centers of chirality in positions 4a and 10b Numbering:

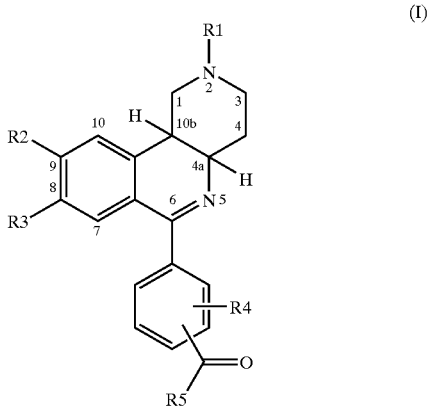

(I)

The invention therefore includes all conceivable pure diastereomers and pure enantiomers and mixtures thereof in any mixing ratio, including the racemates. Preference is given to compounds of the formula I in which the hydrogen atoms in positions 4a and 10b are in the cis position relative to one another. The pure cis enantiomers and their mixtures in any mixing ratio and including the racemates are particularly preferred.

Particularly preferred in this context are those compounds of the formula I which in positions 4a and 10b have the same absolute configuration as the compound (−)-cis-4-amino-3-(3-ethoxy-4-methoxyphenyl)-1-methylpiperidine dihydrochloride having the optical rotation $[\alpha]_D^{20}=-65.50°$ (c=1, methanol) which can be employed as a starting material and is described in WO99/57118.

The enantiomers can be separated in a known manner (for example by preparing and separating corresponding diastereoisomeric compounds) or by stereoselective synthesis methods. Such separation processes and synthesis methods are described, for example, in EP 247 971 and in DE42 17 401.

The compounds according to the invention can be prepared, for example, as shown in the reaction schemes below.

Reaction scheme 1: In a first reaction step, compounds of the formula VII, in which R1, R2 and R3 have the meanings given above, are reacted with compounds of the formula VI, in which R4 has the meaning given above, R is, for example, 1–4C-alkyl and X is a suitable leaving group, for example a chlorine atom. This benzoylation is carried out, for example, according to the Einhorn process, the Schotten-Baumann variant or as described in J. Chem. Soc. C, 1971, 1805–1808.

The preparation of cis/trans racemate mixtures and of pure cis racemates of compounds of the formula VII is described, for example, in U.S. Pat. No. 3,899,494, in DE-A 21 23 328 and in DE-A 16 95 782. Pure cis enantiomers of the compounds of the formula VII can be obtained, for example, by the processes disclosed in EP 0 247 971 and in DE 42 17 401.

Compounds of the formula VI are known or can be prepared by known processes such as, for example, the process shown in reaction scheme 2.

The compounds of the formula IV are obtained by cyclocondensation of the compounds of the formula V obtained in the first reaction step.

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxytrichloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling point of the solvent or condensing agent used.

Starting with the compounds of the formula IV, the compounds of the formula I can be obtained by different routes. On the one hand, the compounds of the formula I can be obtained from the compounds of the formula IV by direct reaction with compounds of the formula R5-H.

Reaction Scheme 1:

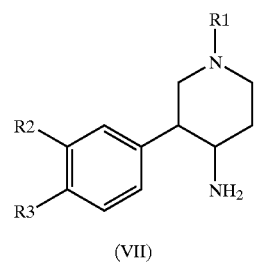

(VII)

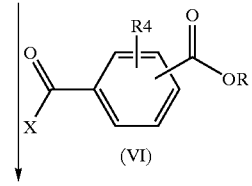

(VI)

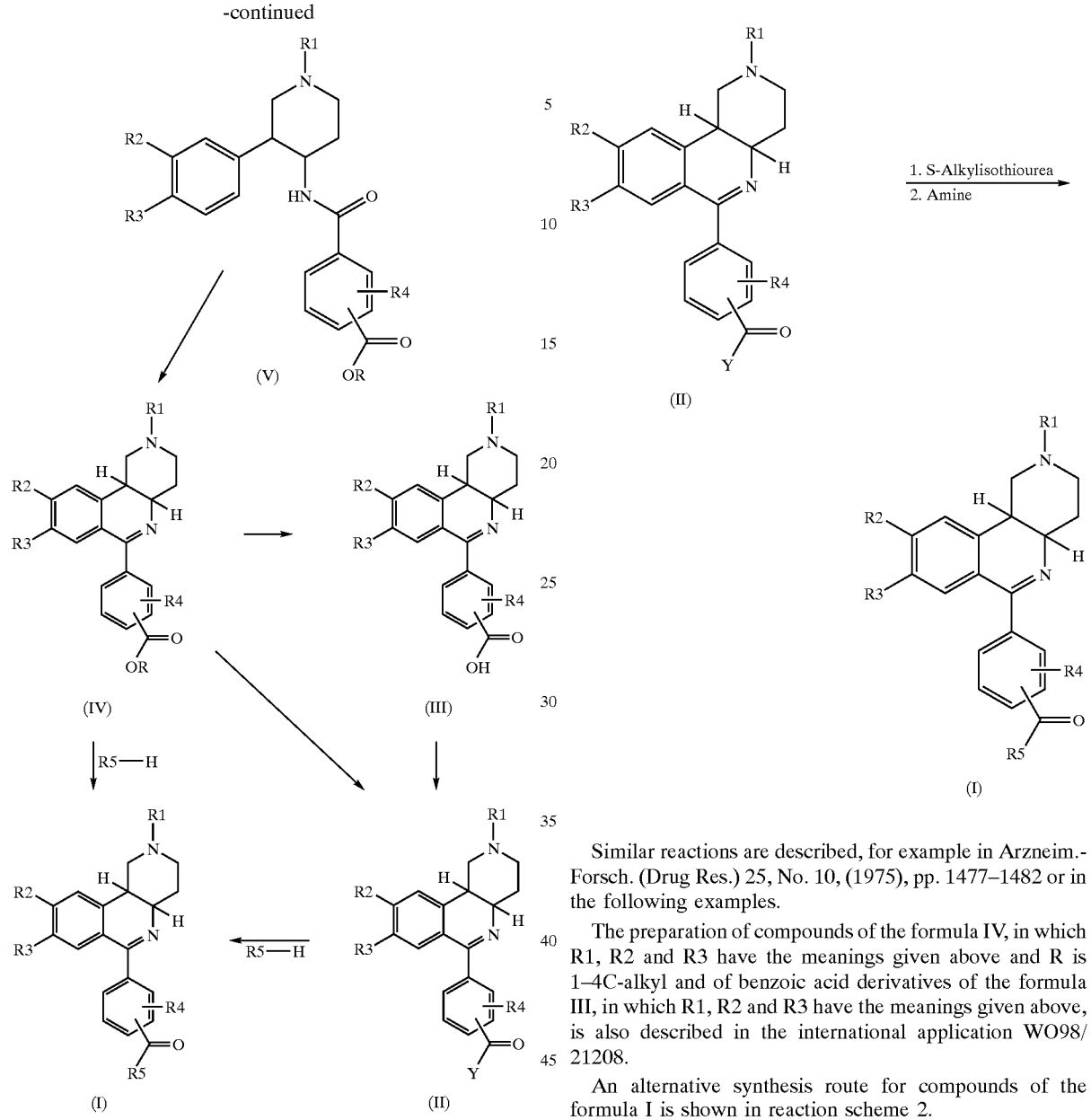

Furthermore, it is possible to additionally activate the benzoic acid derivatives of the formula III prior to the reaction with compounds of the formula R5-H, for example by forming an acid halide or acid anhydride, or by using coupling agents known to the person skilled in the art, such as, for example, N,N'-dicyclohexylcarbodiimide or N'-(3-dimethylaminopropyl)-N-ethylcarbodiimide (compounds of the formula II).

It is also possible to obtain compounds of the formula I from compounds of the formula II by initially reacting the compounds of the formula II in which Y is, for example, a chlorine atom with suitably substituted S-alkyl-isothioureas and then, in a second step, replacing the S-alkyl group by a suitably substituted amine.

Similar reactions are described, for example in Arzneim.-Forsch. (Drug Res.) 25, No. 10, (1975), pp. 1477–1482 or in the following examples.

The preparation of compounds of the formula IV, in which R1, R2 and R3 have the meanings given above and R is 1–4C-alkyl and of benzoic acid derivatives of the formula III, in which R1, R2 and R3 have the meanings given above, is also described in the international application WO98/21208.

An alternative synthesis route for compounds of the formula I is shown in reaction scheme 2.

Starting with a suitably substituted phthalic acid, isophthalic acid or terephthalic acid monoester derivative (compounds of the formula XII), the acid group is initially activated, for example by forming an acid halide (compounds of the formula VI).

Reaction scheme 2:

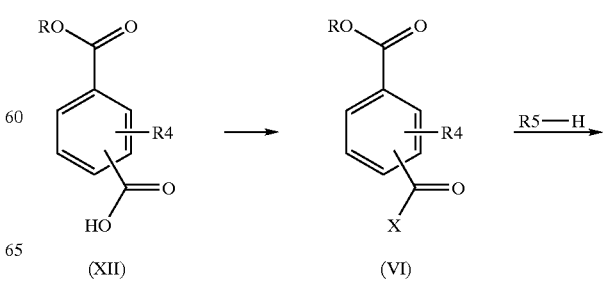

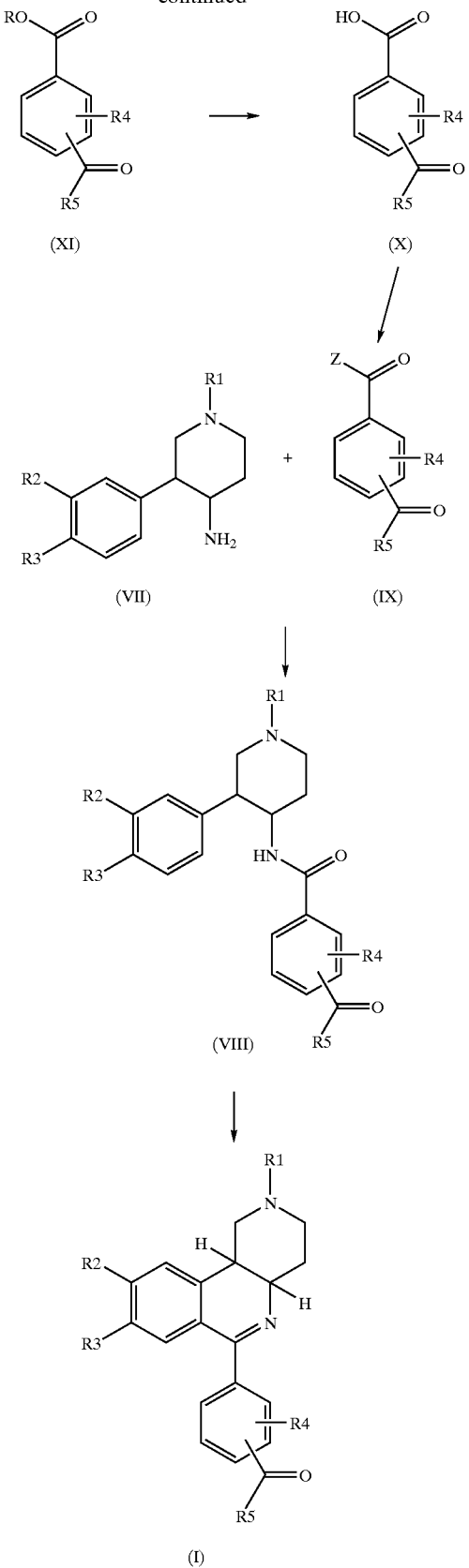

The acid halide (compounds of the formula VI) is then reacted with compounds of the formula R5-H. The ester group of the resulting guanidine derivatives (compounds of the formula XI) is hydrolyzed and the resulting acids (compounds of the formula X) are activated, for example by conversion into an acid halide (compounds of the formula IX).

In the next reaction step, compounds of the formula VII, in which R1, R2 and R3 have the meanings given above are benzoylated with the compounds of the formula IX. Again, this benzoylation is carried out, for example, by the Einhorn process, the Schotten-Baumann variant or as described in J. Chem. Soc. (C), 1971, 1805–1808.

The final cyclocondensation of the compounds of the formula VIII obtained by the benzoylation affords the compounds of the formula I.

The compounds of the formula I prepared by the processes described above can then, if desired, be converted into their salts, or salts of the compounds of the formula I obtained can then, if desired, be converted into the free compounds. Corresponding processes are known to the person skilled in the art.

Suitably substituted phthalic acid, isophthalic acid or terephthalic acid monoester derivatives (compounds of the formula VI or XII) are either known or can be prepared by methods known to the person skilled in the art. Exemplary compounds of the formula VI which may be mentioned are methyl 4-chlorocarbonylbenzoate (preparation described in J. Amer. Chem. Soc. 79, (1957), 96 or in Bioorg. Med. Chem. Lett. 1999, 227–232) and methyl 3-chlorocarbonylbenzoate (preparation described in J. Med. Chem. 1999, 2621–2632).

It is also known to the person skilled in the art that, if a plurality of reactive centers are present in a starting material or intermediate, it may be necessary to temporarily block one or more reactive centers with protective groups so that a reaction takes place only at the desired reactive center. A detailed description of how to use a large number of proven protective groups can be found, for example, in T. W. Greene, Protective Groups in Organic Synthesis, John Wiley & Sons, 1991.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

The following examples serve to illustrate the invention in greater detail without restricting it. Further compounds of the formula I, whose preparation is not explicitly described, can also be prepared in an analogous manner or in a manner familiar per se to the person skilled in the art using customary process techniques.

In the examples, m.p. stands for melting point, h for hour(s), RT for room temperature, EF for empirical formula and MW for molecular weight. The compounds mentioned in the examples and their salts are a preferred subject of the invention.

Examples

End Products 1. 4-[(+)-cis-9-Ethoxy-8-methoxy-2-methyl-1,2,3,4,4a,10b-hexahydro[c][1,6]naphthyridin-yl)-N-(1-imino-1-morpholin-4-ylmethyl)]benzamide dihydrochloride Over a period of about 5 min, a solution of 1.86 g of 4-(cis-9-ethoxy-8-methoxy-2-methyl-1,2,3,4,4a,10b-hexahydrobenzo[c][1,6]naphthyridin-6-yl)benzoyl chloride in 70 ml of acetonitrile is added dropwise to a mixture, cooled with ice/water, of 0.51 g of N-amidinomorpholine and 2 ml of triethylamine in 100 ml of acetonitrile. The reaction mixture is stirred at RT overnight and then substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. The foamed solid residue is dissolved in a little methanol, 2 equivalents of aqueous HCl are added to the solution and this solution is concentrated. This gives 0.84 g of the title compound of m.p. 208–218° C. (unsharp, slow deliquescence).

EF: $C_{28}H_{35}N_5O_4 \times 2HCl$; MW: 578.54.

Optical rotation: $[\alpha]_D^{20}=+107.1°$ (c=10.46 mg/ml, methanol)

Analogously to example 1, the following title compounds are obtained when, instead of N-amidinomorpholine, the respective appropriately substituted guanidines are used as reaction partners:

2. N'-{1-[4-((+)-cis-9-Ethoxy-8-methoxy-2-methyl-1,2,3,4,4a,10b-hexahydro[c][1,6]naphthyridin-6-yl)phenyl]methanoyl}-N,N-diethylguanidine dihydrochloride EF: $C_{28}H_{37}N_5O_3 \times 2HCl$; MW: 564.56; m.p.: 194–203° C. (unsharp, solid foam)

Optical rotation: $[\alpha]_D^{20}=+73.6°$ (c=10.33 mg/ml, methanol)

3. N'{1-[4-((+)-cis-9-Ethoxy-8-methoxy-2-methyl-1,2,3,4,4a,10b-hexahydro[c][1,6[-naphthyridin-6-yl)phenyl]methanoyl}-N,N-dimethylguanidine dihydrochloride EF: $C_{26}H_{33}N_5O_3 \times 2HCl$; MW: 536.51; m.p.: 134–141° C. (unsharp, solid foam)

Optical rotation: $[\alpha]_D^{20}=+25.5°$ (c=9.79 mg/ml, methanol).

The (2R,3R)/(L)-(+)-tartrate of the free base of the title compound has a m.p. 140–146° C.;

EF: $C_{26}H_{33}N_5O_3 \times C_4H_6O_6 \times 1.23H_2O$; MW: 635.90

Optical rotation: $[\alpha]_D^{20}=-41.8°$ (c=10.04 mg/ml, methanol)

4. N'-{1-[4-((+)-cis-9-Ethoxy-8-methoxy-2-methyl-1,2,3,4,4a,10b-hexahydro[c][1,6]naphthyridin-6-yl)phenyl]methanoyl}-N-(2-hydroxyethyl)-N-methylguanidine dihydrochloride EF: $C_{27}H_{35}N_5O_4 \times 2HCl$; MW: 566.53; m.p.: 172–179° C. (unsharp, solid foam)

Optical rotation: $[\alpha]_D^{20}=+51.9°$ (c=10.21 g/ml, methanol)

5. N''{1-[4-((-)-cis-9-Ethoxy-8-methoxy-2-methyl-1,2,3,4,4a,10b-hexahydro[c][1.6]naphthyridin-6-yl)phenyl]methanoyl}-N,N,N',N'-tetramethylguanidine hydrochloride EF: $C_{28}H_{37}N_5O_3 \times HCl$; MW: 528.10; m.p.: 169–175° C. (unsharp, solid foam)

Optical rotation: $[\alpha]_D^2=-44.2°$ (c=9.85 mg/ml, methanol)

6. N-[1-Amino-1-(4-methylpiperazin-1-yl)methylene]-4-((+)-cis-9-ethoxy-8-methoxy-2-methyl-1,2,3,4,4a,10b-hexahydro[c][1,6]naphthyridin-6-yl)benzamide dihydrochloride EF: $C_{29}H_{38}N_6O_3 \times 2HCl$; MW: 591.59; m.p.: 209–215° C. (unsharp)

Optical rotation: $[\alpha]_D^{20}=+9.8°$ (c=9.66 mg/ml, methanol)

7. N-{1-[4-((-)-cis-9-Ethoxy-8-methoxy-2-methyl-1,2,3,4,4a,10b-hexahydro-benzo[c]-[1,6]naphthyridin-6-yl)-phenyl]-methanoyl}guanidine EF: $C_{24}H_{29}N_5O_3$; MW: 435.53; m.p.: 180–190° C. (unsharp, solid foam)

Optical rotation: $[\alpha]_D^{20}=-94.4°$ (c=10.38 mg/ml, methanol)

8. N'-{1-[4-((-)-cis-8,9-Dimethoxy-2-methyl-1,2,3,4,4a,10b-hexahydro-benzo[c][1,6]naphthyridin-6-yl)-phenyl]-methanoyl}-N,N-dimethyl-guanidinehydrochloride EF: $C_{25}H_{31}N_5O_3 \times HCl$; MW: 486.02; m.p.: 188–192° C. (unsharp, solid foam)

Optical rotation: $[\alpha]_D^{20}=65.2°$ (c=9.67 mg/ml, methanol); contains about 25% of the (+)-cis-enanthiomer 9. N''-{1-[4-((-)-cis-8,9-Dimethoxy-2-methyl-1,2,3,4,4a,10b-hexahydro-benzo[c][1,6]naphthyridin-6-yl)-phenyl]-methanoyl}-N,N,N',N'-tetramethyl-guanidine hydrochloride EF: $C_{27}H_{35}N_5O_3 \times HCl \times 1.1H_2O$; MW: 533.95; m.p.: 161–166° C. (unsharp, solid form)

Optical rotation: $[\alpha]_D^{20}=-54°$ (c=10.10 mg/ml, methanol); contains about 25% of the (+)-cis-enantiomer 10. N'-{1-[3-(cis)-9-Ethoxy-8-methoxy-2-methyl-1,2,3,4,4a,10b-hexahydro-benzo[c][c][1,6]naphthyridin-6-yl)-phenyl]-methanoyl}-N,N-dimethyl-guanidine EF: $C_{26}H_{33}N_5O_3$; MW: 463.59; m.p.: 186–188° C. (unsharp, solid foam)

11. 4-((cis)-9-Ethoxy-8-methoxy-2-methyl-1,2,3,4,4a,10b-hexahydro-benzo[c][1,6]naphthyridin-6-yl)-N-(1-imino-1-pyrrolidin-1-yl-methyl)-benzamide EF: $C_{28}H_{35}N_5O_3$; MW: 489.6; m.p.: 145–152° C. (unsharp, solid foam)

12. N-{1-[4(cis)-8,9-Dimethoxy-2-methyl-1,2,3,4,4a,10b-hexahydro-benzo[c][1,6]naphthyridin-6-yl)-phenyl]-methanoyl}-guanidine EF: $C_{23}H_{27}N_5O_3$; MW: 421.50; m.p.: 151–155° C. (unsharp, solid foam)

13. N'-{1-[4-((cis)-9-Ethoxy-8-methoxy-2-methyl-1,2,3,4,4a,10b-hexahydro-benzo[c][1,6]naphthyridin-6-yl)-phenyl]-methanoyl}-N,N,N''-trimethyl-guanidine hydrochloride EF: $C_{27}H_{35}N_5O_3 \times HCl$; MW: 514.07; m.p.: 143–150° C. (unsharp, solid foam)

14. N-{1-[4-((-)-cis-9-Ethoxy-8-methoxy-2-methyl-1,2,3,4,4a,10b-hexahydro-benzo[c][1,6]naphthyridin-6-yl)-phenyl]-methanoyl}-N'-methyl-guanidine EF: $C_{25}H_{31}N_5O_3$; MW: 449.56; m.p.: 160–168° C. (unsharp, solid foam)

Optical rotation: $[\alpha]_D^{20}=-71.40$ (c=9.87 mg/ml, methanol)

15. N-{1-[4-((-)-cis-9-Ethoxy-8-methoxy-2-methyl-1,2,3,4,4a,10b-hexahydro-benzo[c][1,6]naphthyridin-6-yl)-phenyl]-methanoyl}-N'-isopropyl-guanidine A suspension of 0.5 g 1-{1-[4-(-)-cis-9-Ethoxy-8-methoxy-2-methyl-1,2,3,4,4a,10bhexahydro-[c][1,6]naphthyridin-6-yl)-phenyl]-methanoyl}-2-methyl-isothiourea and 0.9 ml isopropylamine in a mixture of 30 ml acetonitril and 30 ml dimethylformamide is stirred at 60° C. for 6 h. The brownish yellow solution is concentrated in vacuo and the brown residue is dissolved in 100 ml of dichloromethan. The organic phase is washed successively with saturated aqueous NaHCO$_3$ (30 ml each) three times, dried over Na$_2$SO$_4$ and concentrated in vacuo to give 0.6 g of the titel compound as a soft foam.

EF: C$_{27}$H$_{35}$N$_5$O$_3$; MW: 477.61; m.p.: 111–114° C. (unsharp, solid foam)

Optical rotation: $[\alpha]_D^{20}$=−71.4° (c=9.87 mg/ml, methanol)

Analogously to example 15, the following title compounds are obtained when, instead of isopropylamine, the respective appropriately substituted amines are used as reaction partners:

16. N-{1-[4-((−)-cis-9-Ethoxy-8-methoxy-2-methyl-1,2,3,4,4a,10b-hexahydro-benzo[c][1,6]naphthyridin-6-yl)-phenyl]-methanoyl}-N'-propyl-guanidine EF: C$_{27}$H$_{35}$N$_5$O$_3$; MW: 477.61; m.p.: 106–108° C. (solid foam)

Optical rotation: $[\alpha]_D^{20}$=−92.2° (c=10.09 mg/ml, methanol)

17. N-{1-[4-((−)-cis-9-Ethoxy8-methoxy-2-methyl-1,2,3,4,4a,10b-hexahydro-benzo[c][1,6]naphthyridin-6-yl)-phenyl]-methanoyl}-N'-isobutyl-guanidine EF: C$_{28}$H$_{37}$N$_5$O$_3$; MW: 491.64; m.p.: 98–100° C. (solid foam)

Optical rotation: $[\alpha]_D^{20}$=−83.0° (c=9.94 mg/ml, methanol)

18. N-{1-[4-((−)-cis-9-Ethoxy-8-methoxy-2-methyl-1,2,3,4,4a,10b-hexahydro-benzo[c][1,6]naphthyridin-6-yl)-phenyl]-methanoyl}-N'-ethyl-guanidine EF: C$_{26}$H$_{33}$N$_5$O$_3$; MW: 463.58; m.p.: 98–100° C. (solid foam)

Optical rotation: $[\alpha]_D^{20}$=−85.0° (c=10.30 mg/ml, methanol)

19. N-Cyclohexyl-N'-{1-[4-((−)-cis-9-ethoxy-8-methoxy-2-methyl-1,2,3,4,4a,10b-hexahydro-benzo [c][1,6] naphthyridin-6-yl)-phenyl]-methanoyl}-guanidine EF: C$_{30}$H$_{39}$N$_5$O$_3$; MW: 517.68; m.p.: 86–90° C. (unsharp,solid foam)

Optical rotation: $[\alpha]_D^{20}$=−76.8° (c=10.16 mg/ml, methanol)

20. N-Cyclohexylmethyl-N'-{1-[4-((−)-cis-9-ethoxy-8-methoxy-2-methyl-1,2,3,4,4a,10b-hexahydro-benzo[c][1,6]naphthyridin-6-yl)-phenyl]-methanoyl}-guanidine EF: C$_{31}$H$_{41}$N$_5$O$_3$; MW: 531.70; m.p.: 93–96° C. (unsharp, solid foam)

Optical rotation: $[\alpha]_D^{20}$=−73.3° (c=9.82 mg/ml, methanol)

21. N-Butyl-N'-{1-[4-((−)-cis-9-ethoxy-8-methoxy-2-methyl-1,2,3,4,4a,10b-hexahydro-benzo[c][1,6] naphthyridin-6-yl)-phenyl]-methanoyl}-guanidine EF: C$_{28}$H$_{37}$N$_5$O$_3$; MW: 491.64; m.p.: 77–79° C. (unsharp, solid foam)

Optical rotation: $[\alpha]_D^{20}$=−83.50 (c=9.82 mg/ml, methanol)

22. N'-{1-[4-((−)-cis-9-Ethoxy-8-methoxy-2-methyl-2-oxy-1,2,3,4,4a,10b-hexahydro-benzo[c][1,6]naphthyridin-6-yl)-phenyl]-methanoyl}-N,N-dimethyl-guanidine 1.2 ml of 30% aqueous hydrogenperoxide are added to a solution of 0.5 g of N'-{1-[4-((−)-cis-9-ethoxy-8-methoxy-2-methyl-1,2,3,4,4a,10b-hexahydro[c][1,6]naphthyridin-6-yl)phenyl]methanoyl)-N,N-dimethylguanidine (free base of title compound of example 3) in 20 ml of methanol at RT and the mixture is stirred for 2 days. The reaction is quenched by adding of 2 g Na$_2$SO$_3$. The resulting suspension is filtered and the filtrate concentrated in vacuo. The residue is dissolved in 50 ml of dichloromethane and the organic phase is washed successively with saturated aqueous NaHCO$_3$ (20 ml each) three times, dried over Na$_2$SO$_4$ and concentrated in vacuo to give 0.2 g of the titel compound as a yellow solid foam.

EF: C$_{26}$H$_{33}$N$_5$O$_3$; MW: 479.58; m.p.: 220–224° C.

Optical rotation: $[\alpha]_D^{20}$=−106.0° (c=9.95 mg/ml, methanol)

Starting Materials

A. 4-(cis-9-Ethoxy-8-methoxy-2-methyl-1,2,3,4,4a,10b-hexahydrobenzo[c][1,6]naphthyridin-6-yl)benzoyl chloride dihydrochloride The title compound is obtained from 4-((−)-cis-9-ethoxy-8-methoxy-2-methyl-1,2,3,4,4a,10b-hexahydro-benzo[c][1,6]naphthyridin-6-yl)benzoic acid by the reaction, known to the person skilled in the art, with a chlorinating agent, such as thionyl chloride, oxalyl chloride, phosphorus trichloride or phosphorus pentachloride. The resulting acid chloride is directly used for the further reaction, without further purification.

B. 1-{1-[4-(−)-cis-9-Ethoxy-8-methoxy-2-methyl-1,2,3,4,4a,10b-hexahydro-benzo[c]naphthyridin-6-yl)-phenyl]-methanoyl}-2-methyl-isothiourea Over a period of about 5 min at RT, 12.3 g O-benzotriazol-1-yl-tetramethyluronium hexafluorophosphate are added to a suspension of 9.86 g 4-((−)-cis-9-Ethoxy-8-methoxy-2-methyl-1,2,3,4,4a,10b-hexahydro-benzo[c][1,6] naphthyridin-6-yl)benzoic acid in 250 ml of acetonitrile and 22 ml diisopropyl-ethylamine. The reaction mixture is stirred 2 hours. Under nitrogen atmosphere the resulting brown solution is added over a period of about 90 min to a suspension prepared from 5.2 g S-methyl-isothiourea sulfate in 150 ml of acetonitrile and 22 ml diisopropyl-ethylamine. The brownish yellow suspension is stirred at RT overnight and then filtered. The light brown residue is washed twice with 50 ml of acetonitrile and dried under reduced pressure. The crude product is used without further purification. This gives 11 g of the title compound of m.p. 199–201° C. (slow deliquescence).

EF: C$_{25}$H$_{30}$N$_3$O$_3$S; MW: 466.61.

Optical rotation: $[\alpha]_D^{20}$=−85.8.1° (c=9.67 mg/ml, methanol)

C. 4-((−)-cis-9-Ethoxy-8-methoxy-2-methyl-1,2,3,4,4a,10b-hexahydrobenzo[c][1,6]naphthyridin-6-yl)benzoic acid The title compound is prepared as described in WO98/21208;

Optical rotation: $[\alpha]_D^{20}$=−109.7° (c=1, methanol+1.0 equivalent 0.1 N aq. sodium hydroxid)

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating action and cilia-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumour necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherence proteins (e.g. integrins). The compounds according to the invention have smooth muscle-relaxant action, e.g. in the region of the bronchial system, of the blood circulation, and of the efferent urinary passages. Furthermore, they have cilia frequency-increasing action, for example in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) respiratory disorders of various origins (bronchitis, allergic bronchitis, bronchial asthma, emphysema, COPD); disorders associated with impaired cilia function or increased demands on ciliar clearance (bronchitis, mucoviscidosis), dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origins such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as antithrombotic, platelet aggregation-inhibiting substances.

The invention further relates to a method for the treatment of mammals including humans who are suffering from one of the abovementioned diseases. The method comprises administering a therapeutically effective and pharmacologically acceptable amount of one or more of the compounds according to the invention to the sick mammal.

The invention further relates to the compounds according to the invention for use in the treatment and/or prophylaxis of diseases, in particular the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

A further subject of the invention is a commercial product, consisting of a customary secondary pack, a primary pack containing the medicament (for example an ampoule or a blister pack) and, if desired, an information leaflet, the medicament exhibiting antagonistic action against cyclic nucleotide phosphodiesterases of types 3 and 4 and leading to the attenuation of the symptoms of illnesses which are connected with cyclic nucleotide phosphodiesterases of types 3 and 4, and the suitability of the medicament for the prophylaxis or treatment of illnesses which are connected with cyclic nucleotide phosphodiesterases of types 3 and 4 being indicated on the secondary pack and/or on the information leaflet of the commercial product, and the medicament containing one or more compounds of the formula I according to the invention. The secondary pack, the primary pack containing the medicament and the information leaflet otherwise comply with what would be regarded as standard to the person skilled in the art for medicaments of this type.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta-mimetics. In combination, on account of their cAMP degradation-inhibiting action, they in this case display a synergistic, superadditive activity. This comes to bear, for example, in their use in combination with PGE2 for the treatment of pulmonary hypertension.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointment bases and other active compound excipients, it is possible to use, for example, antioxidants, dispersants, emulsifiers, preservatives, solubilizers or permeation promoters.

For the treatment of diseases of the respiratory tract, the compounds according to the invention are preferably also administered by inhalation, preferably in the form of an aerosol, with the aerosol particles of solid, liquid or mixed composition having a diameter of from 0.5 to 10 µm, advantageously of from 2 to 6 µm.

The aerosol can be produced, for example, using pressure-driven nozzle nebulizers or ultrasonic nebulizers, advantageously, however, using propellant gas-driven metered aerosols or by means of the propellant gas-free use of micronized active compounds from inhalation capsules.

Depending on the inhalation system employed, the administration forms also contain, in addition to the active compounds, the requisite auxiliary substances, for example propellant gases (e.g. Frigen in the case of metered aerosols), surface-active substances, emulsifiers, stabilizers, preservatives, aromatizing agents, fillers (e.g. lactose in the case of powder inhalers) and, where appropriate, additional active compounds.

For the purposes of inhalation, there are available a large number of appliances which can be used to generate aerosols of optimal particle size and administer them using an inhalation technique which is as appropriate as possible for the patient. In addition to using attachments (spacers and expanders) and pear-shaped containers (e.g. Nebulator® and Volumatic®), and also automatic spray puff releasers (Autohaler®) for metered aerosols, a number of technical solutions are available, particularly in the case of the powder inhalers (e.g. Diskhaler®, Rotadisk®, Turbohaler® or the inhaler described in European patent application 0 505 321), which technical solutions can be used to achieve optimal administration of the active compound.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg per kilogram per day.

Biological Investigations

The second messenger cyclic AMP (cAMP) is known for inhibiting inflammatory cells and cells responsible for the immunological response. The PDE4 isoenzyme is widely distributed in cells associated with the initiation and spreading of inflammatory diseases (H Tenor and C Schudt, in "Phosphodiesterase Inhibitors", 21–40, "The Handbook of Immunopharmacology", Academic Press 1996); its inhibition results in the increase of the intracellular cyclic AMP concentration and thus in the inhibition of cellular activation (J E Souness et al., Immunopharmacology 47: 127–162, 2000).

The anti-inflammatory potential of PDE4 inhibitors in vivo has been described in various animal models (MMTeixeira, TIPS 18: 164–170, 1997). To examine the PDE4 inhibition on a cellular level (in vitro), a large number of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor alpha (TNFα) in monocytes, macrophages or dendritic cells (Gantner et al., Brit J Pharmacol 121: 221–231, 1997 and Pulmonary Pharmacol Therap 12: 377–386, 1999). The immunomodulatory potential of the PDE4 inhibitors furthermore becomes apparent by inhibition of T-cell responses such as cytokine synthesis or proliferation (D M Essayan, Biochem Pharmacol 57: 965–973, 1999). PDE4 inhibition by the substances according to the invention is thus a central indicator of the suppression of inflammatory processes.

Some of the cells involved in inflammatory processes contain, in addition to PDE4, also the PDE3 isoenzyme which likewise contributes to the total cAMP metabolism of these cells. Examples are endothelial cells, mast cells, T-cells, macrophages and dendritic cells. In these cell types, the inhibitory action of PDE4 inhibitors can be enhanced by additional PDE3 inhibition. In the case of (respiratory) smooth muscle cells, inhibition of the PDE3 activity is furthermore important for (broncho)relaxation (A Hatzelmann et al., in "Phosphodiesterase Inhibitors", 147–160, "The Handbook of Immunopharmacology", Academic Press, 1996).

A. Methodology

1. Inhibition of PDE Isoenzymes

The PDE activity was determined according to Thompson et al. (Adv Cycl Nucl Res 10: 69–92, 1979) with some modifications (Bauer and Schwabe, Naunyn-Schmiedeberg's Arch Pharmacol 311: 193198, 1980). The test samples contained 20 mM Tris (pH 7.4), 5 mM $MgCl_2$, 0.5 µM cAMP or cGMP, [$^3$H]cAMP or [$^3$H]cGMP (about 30 000 cpm/sample), the PDE isoenzyme-specific additives described in greater detail below, the indicated concentrations of inhibitor and an aliquot of the enzyme solution in a total sample volume of 200 µl. Dilution series of the compounds according to the invention were prepared in DMSO and further diluted in the samples [1:100 (v/v)], to give the desired end concentration of the inhibitors at a DMSO concentration of 1% (v/v), which for its part has only a minute effect on PDE activity.

After preincubation at 37° C. for 5 minutes, the reaction was started by addition of the substrate (cAMP or cGMP). The samples were incubated at 37° C. for a further 15 min. The reaction was terminated by addition of 50 µl 0.2 N HCl. After cooling on ice for 10 minutes and addition of 25 µg 5'-nucleotidase (snake venom from Crotalus atrox), the mixture was again incubated at 37° C. for 10 min and the samples were then applied to QAE Sephadex A-25 columns (sample volume 1 ml). The columns were eluted with 2 ml of 30 mM ammonium formate (pH 6.0). The radioactivity of the eluate was measured and corrected by the corresponding blank values (measured in the presence of denatured protein); the blank values were less than 5% of the total radioactivity. In no case did the proportion of hydrolyzed nucleotide exceed 30% of the original substrate concentration.

PDE3 (cGMP-inhibited) was investigated in homogenates of human platelets (see Schudt et al., Biochem Pharmacol 1991: 42, 153–162) using cAMP or cGMP as substrate.

PDE4 (cAMP-specific) was investigated in the cytosol of human polymorphonuclear leukocytes (PMNL) [isolated from leukocyte concentrates, see Schudt et al., Arch Pharmacol 1991: 344, 682–690] using cAMP as substrate. The PDE3 inhibitor motapizone (1 μM) was used to suppress the PDE3 activity emanating from contaminated platelets.

The $IC_{50}$ values were determined from the concentration-inhibition curves by nonlinear regression.

B. Results

In table 1 below, the inhibitory concentrations according to section A1 [inhibitory concentrations as -log $IC_{50}$ (mol/l)] are indicated for a number of compounds according to the invention for the PDE4 and the PDE3 isoenzyme. The number of the compounds corresponds to the numbers of the examples in the section End products.

TABLE 1

| Compound | PDE4 [-log $IC_{50}$, mol/l] | PDE3 |
|---|---|---|
| 1 | 9.22 | 6.87 |
| 2 | 9.77 | 7.37 |
| 3 | 9.39 | 7.06 |
| 4 | 8.34 | 5.94 |
| 5 | 9.01 | 6.89 |
| 6 | 9.13 | 6.44 |
| 7 | 8.83 | 6.71 |
| 10 | 8.15 | 6.05 |
| 11 | 8.41 | 6.26 |
| 13 | 9.34 | 7.04 |
| 14 | 8.82 | 6.51 |
| 15 | 9.11 | 6.81 |
| 16 | 9.65 | 6.78 |
| 17 | 9.34 | 6.91 |
| 18 | 8.76 | 6.61 |
| 19 | 9.50 | 6.88 |
| 20 | 9.65 | 7.01 |
| 21 | 9.49 | 6.89 |
| 22 | 7.71 | 6.17 |

What is claimed is:

1. A compound of the formula I, (I)

in which

R1 is 1–4C-alkyl,

R2 is hydroxyl, 1–4C-alkoxy, 3–7C-cycloalkoxy, 3–7C-cycloalkylmethoxy, or 1–4C-alkoxy which is completely or predominantly substituted by fluorine, R3 is hydroxyl, 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–20-alkylenedioxy group, R4 is hydrogen, halogen, nitro, 1–4C-alkyl, trifluoromethyl or 1–4C-alkoxy, R5 is a radical of the formula (a), (b) or (c)

(a)

(b)

(c)

in which if R5 is a radical of the formula (b), either

R6, R7, R8 and R9 independently of one another are hydrogen, 1–7C-alkyl, 3–7C-cycloalkyl, 3–7-cycloalkylmethyl or hydroxy-2–4-C-alkyl, or R6 is hydrogen, 1–7C-alkyl, 3–7C-cycloalkyl, 3–7-cycloalkylmethyl or hydroxy-2–4-C-alkyl, R7 is hydrogen, 1–7C-alkyl, 3–7C-cycloalkyl, 3–7-cycloalkylmethyl or hydroxy-2–4-C-alkyl, R8 and R9, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, in which if R5 is a radical of the formula (c), either R10, R11, R12 and R13 independently of one another are hydrogen, 1–7C-alkyl, 3–7C-cycloalkyl, 3–7-cycloalkylmethyl or hydroxy-2–4-C-alkyl, or R10 and R11 independently of one another are hydrogen, 1-7C-alkyl, 3–7C-cycloalkyl, 3–7-cycloalkylmethyl or hydroxy-2–4-C-alkyl, and R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, or R10 and R11, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, and R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, or R10 and R13 independently of one another are hydrogen or 1–4C-alkyl, and R and R12, together and including the N—C(=)—N structure to which they are bonded, are a hexahydropyrimidin-2-ylidene or imidizolidin-2-ylidene radical, or a salt, solvate, hydrate, solvate of a salt, hydrate of a salt, N-oxide, enantiomer, E/Z isomer or tautomer thereof, or a salt of an N-oxide, enantiomer, E/Z isomer or tautomer thereof.

2. A compound of the formula I as claimed in claim 1, in which

R1 is 1–4C-alkyl,
R2 is hydroxyl, 1–4C-alkoxy, 3–7C-cycloalkoxy, 3–7C-cycloalkylmethoxy, or 1–4C-alkoxy which is completely or predominantly substituted by fluorine,
R3 is hydroxyl, 1–4C-alkoxy, 3–7C-cycloalkoxy, 3–7C-cycloalkylmethoxy, or 1–4C-alkoxy which is completely or predominantly substituted by fluorine,
or in which
R2 and R3 together are a 1–2C-alkylenedioxy group,
R4 is hydrogen, halogen, nitro, 1–4C-alkyl, trifluoromethyl or 1–4C-alkoxy,
R5 is a radical of the formula (a), (b) or (c)

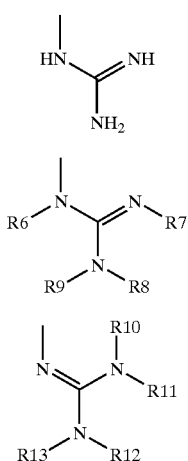

in which
if R5 is a radical of the formula (b), either
R6, R7, R8 and R9 independently of one another are hydrogen, 1–7C-alkyl, 3–7C-cycloalkyl, 3–7-cycloalkylmethyl or hydroxy-2–4-C-alkyl, or
R6 is hydrogen, 1 –7C-alkyl, 3–7C-cycloalkyl, 3–7-cycloalkylmethyl or hydroxy-2–4-C-alkyl,
R7 is hydrogen, 1–7C-alkyl, 3–7C-cycloalkyl, 3–7-cycloalkylmethyl or hydroxy-2–4-C-alkyl,
R8 and R9, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical,
in which
if R5 is a radical of the formula (c), either
R10, R11, R12 and R13 independently of one another are hydrogen, 1–7C-alkyl, 3–7C-cycloalkyl, 3–7-cycloalkylmethyl or hydroxy-2–4-C-alkyl, or
R10 and R11 independently of one another are hydrogen, 1–7C-alkyl, 3–7C-cycloalkyl, 3–7-cycloalkylmethyl or hydroxy-2–4-C-alkyl, and
R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, or
R10 and R11, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, and
R12 and R13, together and including the nitrogen atom to which both are bonded, are a 1-pyrrolidinyl, 1-piperidinyl, 1-hexahydroazepinyl, 4-morpholinyl or 4-(1–4C-alkyl-)-piperazin-1-yl radical, or R10 and R13 independently of one another are hydrogen or 1–4C-alkyl, and
R11 and R12, together and including the N—C(=)—N structure to which they are bonded, are a hexahydropyrimidin-2-ylidene or imidizolidin-2-ylidene radical,
or a salt, solvate, hydrate, solvate of a salt, hydrate of a salt, enantiomer, E/Z isomer or tautomer thereof,
or a salt of an enantiomer, E/Z isomer or tautomer thereof.
3. A compound of the formula I as claimed in claim 1, in which
R1 is 1–4C-alkyl,
R2 is 1–4C-alkoxy, 3–6C-cycloalkoxy, 3–6C-cycloalkylmethoxy, or 1–4C-alkoxy which is completely or predominantly substituted by fluorine,
R3 is 1–4C-alkoxy, 3–6C-cycloalkoxy, 3–6C-cycloalkylmethoxy, or 1–4C-alkoxy which is completely or predominantly substituted by fluorine,
R4 is hydrogen, halogen, nitro, 1–4C-alkyl, trifluoromethyl or 1–4C-alkoxy,
R5 is a radical of the formula (a), (b) or (c)

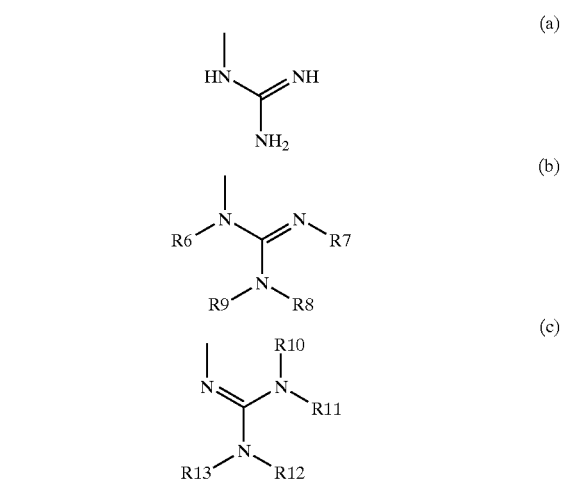

in which
if R5 is a radical of the formula (b), either
R6 is hydrogen, and
R7, R8 and R9 independently of one another are hydrogen, 1–4C-alkyl, 3–7C-cycloalkyl, 3–7-cycloalkylmethyl or hydroxy-2–4-C-alkyl, or
R6 is hydrogen,
R7 is hydrogen, 1–4C-alkyl, 3–7C-cycloalkyl or 3–7C-cycloalkylmethyl, and
R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical,
in which
if R5 is a radical of the formula (c), either
R10, R11, R12 and R13 independently of one another are hydrogen, 1–4C-alkyl, 3–7C-cycloalkyl, 3–7-cycloalkylmethyl or hydroxy-2–4-C-alkyl, or
R10 and R11 independently of one another are hydrogen, 1–4C-alkyl, 3–7C-cycloalkyl, 3–7-cycloalkylmethyl or hydroxy-2–4-C-alkyl, and
R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R13 independently of one another are hydrogen or 1–4C-alkyl, and R11 and R12, together and including the N—C(=)—N structure to which they are bonded, are a hexahydropyrimidin-2-ylidene or imidizolidin-2-ylidene radical, or a salt, solvate, hydrate, solvate of a salt, hydrate of a salt, N-oxide, enantiomer, E/Z isomer or tautomer thereof, or a salt of an N-oxide, enantiomer, E/Z isomer or tautomer thereof.

4. A compound of the formula I as claimed in claim 1, in which

R1 is 1–4C-alkyl,

R2 is 1–4C-alkoxy, 3–6C-cycloalkoxy, 3–6C-cycloalkylmethoxy, or 1–4C-alkoxy which is substituted by fluorine, R3 is 1–4C-alkoxy, 3–6C-cycloalkoxy, 3–6C-cycloalkylmethoxy, or 1–40-alkoxy which is substituted by fluorine, R4 is hydrogen, halogen, nitro, 1–4C-alkyl, trifluoromethyl or 1–4C-alkoxy, R5 is a radical of the formula (a), (b) or (c)

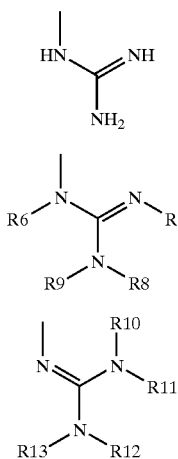

in which if R5 is a radical of the formula (b), either

R6 is hydrogen, and

R7, R8 and R9 independently of one another are hydrogen, 1–4C-alkyl, 3–7C-cycloalkyl, 3–7-cycloalkylmethyl or hydroxy-2–4-C-alkyl, or R6 is hydrogen, R7 is hydrogen, 1–4C-alkyl, 3–7C-cycloalkyl or 3–7C-cycloalkylmethyl, and R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, in which if R5 is a radical of the formula (c), either R10, R11, R12 and R13 independently of one another are hydrogen, 1–4C-alkyl, 3–7C-cycloalkyl, 3–7-cycloalkylmethyl or hydroxy-2–4C-alkyl, or R10 and R11 independently of one another are hydrogen, 1–4C-alkyl, 3–7C-cycloalkyl, 3–7-cycloalkylmethyl or hydroxy-2–4-C-alkyl, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R13 independently of one another are hydrogen or 1–4C-alkyl, and R11 and R12, together and including the N—C(=)—N structure to which they are bonded, are a hexahydropyrimidin-2-ylidene or imidizolidin-2-ylidene radical, or a salt, solvate, hydrate, solvate of a salt, hydrate of salt, enantiomer, E/Z isomer or tautomer thereof, or a salt of an enantiomer, E/Z isomer or tautomer thereof.

5. A compound of the formula I as claimed in claim 1, in which

R1 is methyl,

R2 is 1–4C-alkoxy,

R3 is 1–4C-alkoxy,

R4 is hydrogen,

R5 is a radical of the formula (a), (b) or (c)

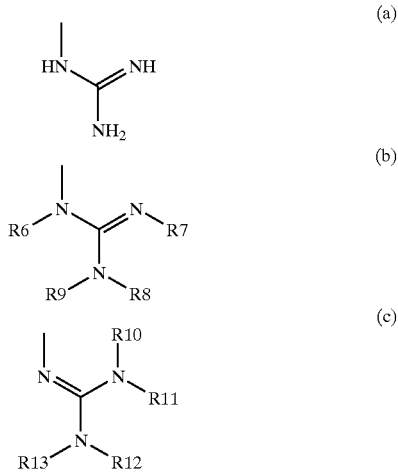

in which if R5 is a radical of the formula (b), either

R6 is hydrogen,

R7 is hydrogen, 1–4C-alkyl, 3–7C-cycloalkyl or 3–7-cycloalkylmethyl,

R8 is hydrogen, 1–4C-alkyl, 3–7C-cycloalkyl or 3–7-cycloalkylmethyl,

R9 is hydrogen, 1–4C-alkyl or hydroxy-2–4-C-alkyl, where atleast one of the radicals R7, R8 and R9 is not hydrogen, or R6 is hydrogen, R7 is hydrogen, 1–4C-alkyl, 3–7C-cycloalkyl or 3–7C-cycloalkylmethyl, and R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, in which if R5 is a radical of the formula (c), either R10 is hydrogen or 10–4C-alkyl, R11 is hydrogen, 1–4C-alkyl, 3–7C-cycloalkyl, 3–7-cycloalkylmethyl, R12 is hydrogen, 1–4-C-alkyl, 3–7C-cycloalkyl, 3–7-cycloalkylmethyl, and R13 is hydrogen, 1–4C-alkyl or hydroxy-2–4-C-alkyl, where atleast one of the radicals R10, R11, R12 and R13 is not hydrogen, or R10 is hydrogen or 1–4C-alkyl, R11 is hydrogen, 1–4C-alkyl, 3–7C-cycloalkyl or 3–7-cycloalkylmethyl, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or a salt, solvate, hydrate, solvate of a salt, hydrate of a salt, N-oxide, enantiomer, E/Z isomer or tautomer thereof, or a salt of an N-oxide, enantiomer, E/Z isomer or tautomer thereof.

6. A compound of the formula I as claimed in claim 1, in which

R1 is methyl,

R2 is methoxy or ethoxy,

R3 is methoxy,

R4 is hydrogen,

R5 is N'-(N,N-dimethyl)guanidinyl, N'-(N,N-diethyl)guanidinyl, (morpholine)-4-carboxamidinyl, 4-methylpiperazine-1-carboxamidinyl-, N'-[N-(2-hydroxyethyl)-N-methyl]guanidinyl, N"-(N,N,N',N'-tetramethyl)guanidinyl, N-guanidinyl, N'-(N,N,N"-trimethyl)guanidinyl, N-(N'-methyl)guanidinyl, N-(N'-isopropyl)guanidinyl, N-(N'-propyl)guanidinyl, N-(N'-isobutyl)guanidinyl, N-(N'-ethyl) guanidinyl, N-cyclohexyl-N'-guanidinyl, N-cyclohexylmethyl-N'-guanidinyl, N-butyl-N'-guanidinyl or pyrrolidin-1-carboxamidinyl, or a salt, solvate, hydrate, solvate of a salt, hydrate of a salt, N-oxide, enantiomer, E/Z isomer or tautomer thereof, or a salt of an N-oxide, enantiomer, E/Z isomer or tautomer thereof.

7. A compound, of the formula I as claimed in claim 1, in which

R1 is methyl,

R2 is 1–4C-alkoxy,

R3 is 1–4C-alkoxy,

R4 is hydrogen,

R5 is a radical of the formula (b) or (c)

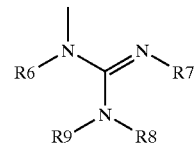

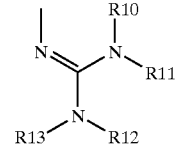

in which if R5 is a radical of the formula (b), either

R6 is hydrogen,

R7 is hydrogen, 1–4C-alkyl, 3–7C-cycloalkyl or 3–7C-cycloalkylmethyl,

R8 is hydrogen, 1–4C-alkyl, 3–7C-cycloalkyl or 3–7C-cycloalkylmethyl, and

R9 is hydrogen, 1–4C-alkyl or hydroxyl-2–4C-alkyl, where atleast one of the radicals R7, R8 and R9 is not hydrogen, or R6 is hydrogen, R7 is hydrogen, 1–4C-alkyl, 3–7C-cycloalkyl or 3–7C-cycloalkylmethyl, and R8 and R9, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, in which if R5 is a radical of the formula (c), either R10 is hydrogen or 1–4C-alkyl, R11 is hydrogen, 1–4C-alkyl, 3–7C-cycloalkyl, 3–7-cycloalkylmethyl, R12 is hydrogen, 1–4C-alkyl, 3–7C-cycloalkyl, 3–7-cycloalkylmethyl, and R13 is hydrogen, 1–4C-alkyl or hydroxy-2–4-C-alkyl, where at least one of the radicals R10, R11, R12 and R13 is not hydrogen, or R10 is hydrogen or 1–4C-alkyl, R11 is hydrogen, 1–4C-alkyl, 3–7C-cycloalkyl or 3–7-cycloalkylmethyl, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or R10 and R11, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, and R12 and R13, together and including the nitrogen atom to which both are bonded, are a 1-pyrrolidinyl, 1-piperidinyl, 1-hexahydroazepinyl, 4-morpholinyl or 4-(1–2C-alkyl)-piperazin-1-yl radical, or a salt, solvate, hydrate, solvate of a salt, hydrate of a salt, enantiomer, E/Z isomer or tautomer thereof, or a salt of an enantiomer, E/Z isomer or tautomer thereof.

8. A compound of the formula I as claimed in claim 1, in which
R1 is methyl,
R2 is methoxy, ethoxy or propoxy,
R3 is methoxy or ethoxy,
R4 is hydrogen,
R5 is N'-(N,N-dimethyl)guanidinyl, N'(N,N-diethyl) guanidinyl, (morpholine)-4-carboxamidinyl, 4-methylpiperazine-1-carboxamidinyl, N'-[N-(2-hydroxyethyl)-N-methyl]guanidinyl, N''-(N,N,N',N'-tetramethyl)guanidinyl,
or a salt, solvate, hydrate, solvate of a salt, hydrate of a salt, enantiomer, E/Z isomer or tautomer thereof,
or a salt of an enantiomer, E/Z isomer or tautomer thereof.

9. A compound of the formula I, selected from the group consisting of
4-[(+)-cis-9-Ethoxy-8-methoxy-2-methyl-1,2,3,4,4a,10b-hexahydro[c][1,6]naphthyridin-6-yl)-N-(1-imino-1-morpholin-4-ylmethyl) ]benzamide,
N'-{1-[4-((+)-cis-9-Ethoxy-8-methoxy-2-methyl-1,2,3,4,4a,10b-hexahydro[c][1,6]naphthyridin-6-yl)-phenyl [methanoyl]-N, N-diethylguanidine,
N'-{1-[4-((+)-cis-9-Ethoxy-8-methoxy-2-methyl-1,2, 3,4,4a,10b-hexahydro[c][1,6]naphthyridin-6-yl)phenyl [methanoyl]-N,N-dimethylguanidine,
N'-{1-[4-((+)-cis-9-Ethoxy-8-methoxy-2-methyl-1,2,3,4,4a,10b-hexahydro[c][1,6]naphthyridin-6-yl)-phenyl [methanoyl]-N-(2-hydroxyethyl)-N-methylguanidine,
N''-(1-[4-((−)-cis-9-Ethoxy-8-methoxy-2-methyl-1,2,3,4,4a,10b-hexahydro[c][1,6]naphthyridin-6-yl)-phenyl] methanoyl}-N,N,N',N'-tetramethylguanidine,
N-[1-Amino-1-(4-methylpiperazin-1-yl)methylene]-4-((+)-cis-9-ethoxy-8-methoxy-2methyl-1,2,3,4, 4a,10b-hexahydro[c][1,6]naphthyridin-6-yl)benzamide,
N-{1-[4-((−)cis-9-Ethoxy-8-methoxy-2-methyl-1,2,3,4,4a,10b-hexahydro-benzo[c][1,6]naphthyridin-6-yl) phenyl]-methanoyl}-guanidine,
N'-(1-[4-((−)-cis-8,9-Dimethoxy-2-methyl-1,2,3,4,4a,10b-hexahydro-benzo[c][1,6]naphthyridin-6-yl) phenyl]-methanoyl}-N,N-dimethyl-guanidine,
N''-{1-[4-((−)-cis-8,9-Dimethoxy-2-methyl-1,2,3,4,4a,10b-hexahydro-benzo[c][1,6]naphthyridin-6-yl) phenyl]-methanoyl}-N,N,N',N'-tetramethyl-guanidine,
N'-(1-[3-(cis)-9-Ethoxy-8-methoxy-2-methyl-1,2, 3,4,4a,10b-hexahydro-benzo[c][1,6]naphthyridin-6-yl) phenyl]-methanoyl}-N,N-dimethyl-guanidine,
4-((cis)-9-Ethoxy-8-methoxy-2-methyl-1,2,3,4,4a,10b-hexahydro-benzo[c][1,6]naphthyridin-6-yl)-N-(11-imino-1-pyrrolidin-1-yl-methyl)-benzamide,
N-(1[-4-(cis)-8,9-Dimethoxy-2-methyl-1,2,3,4,4a,10b-hexahydro-benzo[c][1,6]naphthyridin-6-yl)phenyl]-methanoyl}-guanidine,
N'-(1-[4-((cis)-9-Ethoxy-8-methoxy-2-methyl-1,2,3,4,4a,10b-hexahydro-benzo[c][1,6]naphthyridin-6-yl) phenyl]-methanoyl}-N,N,N''-trimethyl-guanidine,
N-{1-[4-((−)-cis-9-Ethoxy-8-methoxy-2-methyl-1,2,3,4,4a,10b-hexahydro-benzo[c][1,6]naphthyridin-6-yl) phenyl]-methanoyl}-N'-methyl-guanidine,
N-{1-[4-((−)-cis-9-Ethoxy-8-methoxy-2-methyl-1,2,3,4,4a,10b-hexahydro-benzo[c][1,6]naphthyridin-6-yl)-phenyl]-methanoyl}-N'-isopropyl-guanidine,
N-{1-[4-((−)-cis-9-Ethoxy-8-methoxy-2-methyl-1,2,3,4,4a,10b-hexahydro-benzo[c][1,6]naphthyridin-6-yl) phenyl]-methanoyl}-N'-propyl-guanidine,
N-{1-[4-((−)-cis-9-Ethoxy-8-methoxy-2-methyl-1,2,3,4,4a,10b-hexahydro-benzo[c][1,6]naphthyridin-6-yl)-phenyl]-methanoyl}-N'-isobutyl-guanidine,
N-{1-[4-((−)-cis-9-Ethoxy-8-methoxy-2-methyl-1,2,3,4,4a,10b-hexahydro-benzo[c][1,6]naphthyridin-6-yl)-phenyl]-methanoyl}-N'-ethyl-guanidine,
N-Cyclohexyl-N'-{1-[4-((−)-9-ethoxy-8-methoxy-2-methyl-1,2,3,4,4,4a,10b-hexahydro-benzo[c][1,6] naphthyridin-6-yl)-phenyl]-methanoyl}-guanidine,
N-Cyclohexylmethyl-N'-{1-[4-((−)-cis-9-ethoxy-8-methoxy-2-methyl-1,2,3,4,4a,10b-hexahydro-benzo[c] [1,6]naphthyridin-6-yl)-phenyl]-methanoyl}-guanidine,
N-Butyl-N'-{1-[4-((−)-cis-9-ethoxy-8-methoxy-2-methyl-1,2,3,4,4a,10b-hexahydro-benzo[c][1,6] naphthyridin-6-yl)-phenyl]-methanoyl}-guanidine,
N'-{1-[4-((−)-cis-9-Ethoxy-8-methoxy-2-methyl1−2-oxy-2,3,4,4a,10b-hexahydro-benzo[c][1,6] naphthyridin-6-yl)-phenyl]-methanoyl}-N,N-dimethyl-guanidine,
or a salt, solvate, hydrate, solvate of a salt or hydrate of a salt thereof.

10. A compound of the formula I as claimed in claim 1, in which the hydrogen atoms in positions 4a and 10b are in the cis position relative to one another,
or a salt, solvate, hydrate, solvate of a salt, hydrate of a salt, N-oxide, enantiomer, E/Z isomer or tautomer thereof,
or a salt of an N-oxide, enantiomer, E/Z isomer or tautomer thereof.

11. A compound of the formula I as claimed in claim 2, in which the hydrogen atoms in positions 4a and 10b are in the cis position relative to one another,
or a salt, solvate, hydrate, solvate of a salt, hydrate of a salt, enantiomer, E/Z isomer or tautomer thereof,
or a salt of an a enantiomer, E/Z isomer or tautomer thereof.

12. A compound of the formula I as claimed in claim 1 which, in positions 4a and 10b, has the same absolute configuration as the compound (−)-cis-4-amino-3-(3-ethoxy-4-methoxyphenyl)-1-methyl-piperidine dihydrochloride having the optical rotation $[\alpha]^{20}=-65.5°$ (c=1, methanol),
or a salt, solvate, hydrate, solvate of a salt, hydrate of a salt, N-oxide, enantiomer, E/Z isomer or tautomer thereof,
or a salt of an N-oxide, enantiomer, E/Z isomer or tautomer thereof.

13. A compound of the formula I as claimed in claim 2 which, in positions 4a and 10b, has the same absolute configuration as the compound (−)-cis-4-amino-3-(3-ethoxy-4-methoxyphenyl)-1-methyl-piperidine dihydrochloride having the optical rotation $[\alpha]^{20}=-65.5°$ (c=1, methanol),
or a salt, solvate, hydrate, solvate of a salt, hydrate of a salt, enantiomer, E/Z isomer or tautomer thereof,
or a salt of an enantiomer, E/Z isomer or tautomer thereof.

14. A method of treating a disease or disorder in a patient comprising administering to a patient in need thereof a thereapeutically effective amount of a compound of the formula I as claimed in claim 1 or a pharmaceutically acceptable salt, solvate, hydrate, solvate of a salt, hydrate of a salt, N-oxide, enantiomer, E/Z isomer or tautomer thereof, or a pharmaceutically acceptable salt of an N-oxide, enantiomer, E/Z isomer or tautomer thereof wherein the disease or disorder is selected from the group consisting of allergic rhinitis, crohn's disease, ulcerative colitis, rheumatoid arthritis, bronchitis, bronchial asthma, COPD, ARDS, psoriasis, eczema, and combination thereof thereof.

15. A pharmaceutical composition comprising one or more compounds of the formula I as claimed in claim 1 or a pharmaceutically acceptable salt, solvate, hydrate, solvate of a salt, hydrate of a salt, N-oxide, enantiomer, E/Z isomer or tautomer thereof,
or a pharmaceutically acceptable salt of an N-oxide, enantiomer, E/Z isomer or tautomer thereof, together with a pharmaceutically acceptable auxiliary and/or excipient.

16. A method of treating a disease or disorder in a patient comprising administering to a patient in need thereof a thereapeutically effective amount of a compound of the formula I as claimed in claim 1 or a pharmaceutically acceptable salt, solvate, hydrate, solvate of a salt, hydrate of a salt, N-oxide, enantiomer, E/Z isomer or tautomer thereof, or a pharmaceutically acceptable salt of an N-oxide, enantiomer, E/Z isomer or tautomer thereof, wherein the disease or disorder is selected from the group consisting of bronchitis, bronchial asthma, COPD, ARDS, psoriasis, eczema, and combinations thereof.

* * * * *

UNITED STATES PATENT AND TRADEMARK OFFICE
CERTIFICATE OF CORRECTION

PATENT NO. : 6,936,622 B2
DATED : August 30, 2005
INVENTOR(S) : Flockerzi

It is certified that error appears in the above-identified patent and that said Letters Patent is hereby corrected as shown below:

Column 21,
Line 65, please delete "1-20-alkylenedioxy" and replace with -- 1-2C-alkylenedioxy --.

Column 22,
Lines 25-26, 27-28, 29-30, 38-39 and 41, please delete "3-7-cycloalkylmethyl" and replace with -- 3-7C-cycloalkylmethyl --.
Line 58, please delete "R and R12," and replace with -- R11 and R12, --.

Column 23,
Lines 37-38, 39-40, 41-42 and 54, please delete "3-7-cycloalkylmethyl" and replace with -- 3-7C-cycloalkylmethyl --.

Column 24,
Lines 48-49, 61-62 and 64, please delete "3-7-cycloalkylmethyl" and replace with -- 3-7C-cycloalkylmethyl --.

Column 25,
Line 29, please delete "1-40-alkoxy" and replace with -- 1-4C-alkoxy --.
Lines 59-60, please delete "3-7-cycloalkylmethyl" and replace with -- 3-7C-cycloalkylmethyl --.

Column 26,
Lines 4-5, 7, 63-64 and 65-66, please delete "3-7-cycloalkylmethyl" and replace with -- 3-7C-cycloalkylmethyl --.

Column 27,
Line 13, please delete "10-4C" and replace with -- 1-4C --.
Lines 14-15, 16-17 and 23-24, please delete "3-7-cycloalkylmethyl" and replace with -- 3-7C-cycloalkylmethyl --.

Column 28,
Lines 41-42, 43-44 and 50-51, please delete "3-7-cycloalkylmethyl" and replace with -- 3-7C-cycloalkylmethyl --.

Column 29,
Line 7, please delete "N'(N,N-diethyl)" and replace with -- N'-(N,N-diethyl) --.
Line 35, please delete "-2methyl-1,2,3,4," and replace with -- -2-methyl-1,2,3,4, --.

UNITED STATES PATENT AND TRADEMARK OFFICE
CERTIFICATE OF CORRECTION

PATENT NO. : 6,936,622 B2
DATED : August 30, 2005
INVENTOR(S) : Flockerzi

It is certified that error appears in the above-identified patent and that said Letters Patent is hereby corrected as shown below:

Column 30,
Lines 18-19, please delete "-methyll-2-oxy2,3,4,4a,10b-" and replace with
-- -methyl-2-oxy-1,2,3,4,4a,10b- --.
Line 36, please delete "an a enantiomer," and replace with -- an enantiomer, --.

Lines 41 and 51, please delete "$[\alpha]^{20}$" and replace with 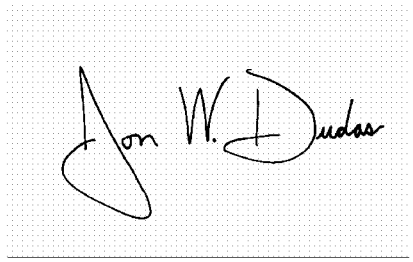

Line 58, please delete "thereapeutically" and replace with -- therapeutically --.
Line 67, please delete "combination thereof thereof" and replace with -- combinations thereof. --.

Column 31,
Line 11, please delete "thereapeutically" and replace with -- therapeutically --.

Signed and Sealed this

Twenty-ninth Day of November, 2005

JON W. DUDAS
*Director of the United States Patent and Trademark Office*